(12) United States Patent
Asmus et al.

(10) Patent No.: US 7,044,921 B2
(45) Date of Patent: May 16, 2006

(54) MEDICAL DEVICE WITH CHANGEABLE TIP FLEXIBILITY

(75) Inventors: Bruce Asmus, Minnetonka, MN (US); Brian Reynolds, Ramsey, MN (US)

(73) Assignee: Scimed Life Systems, INC, Maple Grove, MN (US)

( * ) Notice: Subject to any disclaimer, the term of this patent is extended or adjusted under 35 U.S.C. 154(b) by 280 days.

(21) Appl. No.: 10/357,132

(22) Filed: Feb. 3, 2003

(65) Prior Publication Data

US 2004/0152941 A1 Aug. 5, 2004

(51) Int. Cl.
*A61M 25/00* (2006.01)

(52) U.S. Cl. ........................ 600/585; 128/898; 606/192

(58) Field of Classification Search ................ 128/898; 606/1–51; 600/585; 604/95.01–96, 523–539
See application file for complete search history.

(56) References Cited

U.S. PATENT DOCUMENTS

| | | | |
|---|---|---|---|
| 2,107,810 A | 2/1938 | Wherry | |
| 3,923,280 A * | 12/1975 | Good | 248/405 |
| 4,234,151 A * | 11/1980 | John et al. | 254/98 |
| 4,538,622 A | 9/1985 | Samson et al. | |
| 4,619,274 A | 10/1986 | Morrison | |
| 4,719,924 A | 1/1988 | Crittenden et al. | |
| 4,721,117 A | 1/1988 | Mar et al. | |
| 4,739,768 A | 4/1988 | Engelson | |
| 4,756,642 A * | 7/1988 | Quinn et al. | 405/7 |
| 4,763,647 A | 8/1988 | Gambale | |
| 4,779,628 A | 10/1988 | Machek | |
| 4,811,743 A | 3/1989 | Stevens | |
| 4,846,186 A | 7/1989 | Box et al. | |
| 4,895,168 A | 1/1990 | Machek | |
| 4,971,490 A | 11/1990 | Hawkins | |
| 4,984,581 A | 1/1991 | Stice | |
| 4,991,602 A | 2/1991 | Amplatz et al. | |
| 5,007,434 A | 4/1991 | Doyle et al. | |
| 5,069,226 A | 12/1991 | Yamauchi et al. | |
| 5,095,915 A | 3/1992 | Engelson | |
| 5,111,829 A | 5/1992 | Alvarez de Toledo | |
| 5,143,085 A | 9/1992 | Wilson | |
| 5,178,158 A | 1/1993 | de Toledo | |
| 5,213,111 A | 5/1993 | Cook et al. | |
| 5,230,348 A | 7/1993 | Ishibe et al. | |
| 5,238,004 A | 8/1993 | Sahatjian et al. | |
| 5,259,393 A | 11/1993 | Corso, Jr. et al. | |
| 5,267,574 A | 12/1993 | Viera et al. | |
| 5,299,580 A | 4/1994 | Atkinson et al. | |
| 5,318,584 A * | 6/1994 | Lange et al. | 606/182 |
| 5,341,818 A | 8/1994 | Abrams et al. | |
| 5,402,799 A | 4/1995 | Colon et al. | |
| 5,409,015 A | 4/1995 | Palermo | |
| 5,433,200 A | 7/1995 | Fleischhacker, Jr. | |
| 5,480,382 A * | 1/1996 | Hammerslag et al. | 604/528 |
| 5,484,409 A * | 1/1996 | Atkinson et al. | 604/103.03 |
| 5,488,959 A | 2/1996 | Ales | |
| 5,497,783 A | 3/1996 | Urick et al. | |
| 5,497,785 A | 3/1996 | Viera | |

(Continued)

*Primary Examiner*—Michael F Peffley
*Assistant Examiner*—Henry M Johnson, III
(74) *Attorney, Agent, or Firm*—Crompton, Seager & Tufte, LLC

(57) ABSTRACT

A medical device with a changeable flexibility and a method of using the same. The medical device may include a core member, a tip member, and a tie member. The tip member may be configured to longitudinally shift relative to core member, which may alter the flexibility of the medical device.

37 Claims, 5 Drawing Sheets

U.S. PATENT DOCUMENTS

| | | | |
|---|---|---|---|
| 5,507,729 A | 4/1996 | Lindenberg et al. | |
| 5,613,978 A * | 3/1997 | Harding | 606/181 |
| 5,636,642 A | 6/1997 | Palermo | |
| 5,664,850 A | 9/1997 | Erickson et al. | |
| 5,669,885 A * | 9/1997 | Smith | 606/184 |
| 5,673,707 A | 10/1997 | Chandrasekaran | |
| 5,688,220 A * | 11/1997 | Verin et al. | 600/1 |
| 5,720,300 A | 2/1998 | Fagan et al. | |
| 5,762,615 A * | 6/1998 | Weier | 600/585 |
| 5,769,796 A | 6/1998 | Palermo et al. | |
| 5,772,609 A | 6/1998 | Nguyen et al. | |
| 5,807,279 A | 9/1998 | Viera | |
| 5,836,893 A | 11/1998 | Urick | |
| 5,924,998 A | 7/1999 | Cornelius et al. | |
| 5,931,819 A | 8/1999 | Fariabi | |
| 5,938,623 A * | 8/1999 | Quiachon et al. | 600/585 |
| 5,984,877 A | 11/1999 | Fleischhacker, Jr. | |
| 6,013,019 A * | 1/2000 | Fischell et al. | 600/3 |
| 6,033,720 A | 3/2000 | Stoltze et al. | |
| 6,039,699 A | 3/2000 | Viera | |
| 6,059,738 A | 5/2000 | Stoltze et al. | |
| 6,132,389 A | 10/2000 | Cornish et al. | |
| 6,139,510 A | 10/2000 | Palermo | |
| 6,142,958 A | 11/2000 | Hammarstrom et al. | |
| 6,168,571 B1 | 1/2001 | Solar et al. | |
| 6,227,938 B1 | 5/2001 | Cheetham et al. | |
| 6,287,292 B1 | 9/2001 | Fariabi | |
| 6,296,616 B1 | 10/2001 | McMahon | |
| 6,312,314 B1 | 11/2001 | Cheetham et al. | |
| 6,348,041 B1 | 2/2002 | Klint | |
| 6,352,501 B1 * | 3/2002 | Urick | 600/3 |
| 6,355,016 B1 | 3/2002 | Bagaoisan et al. | |
| 6,375,629 B1 | 4/2002 | Muni et al. | |
| 6,383,146 B1 | 5/2002 | Klint | |
| 6,390,993 B1 | 5/2002 | Cornish et al. | |
| 6,409,683 B1 | 6/2002 | Fonseca et al. | |
| 6,428,489 B1 | 8/2002 | Jacobsen et al. | |
| 6,488,637 B1 | 12/2002 | Eder et al. | |
| 6,502,606 B1 | 1/2003 | Klint | |
| 2003/0006354 A1* | 1/2003 | Biles et al. | 248/354.1 |
| 2003/0050588 A1* | 3/2003 | Slishman | 602/32 |
| 2003/0069520 A1 | 4/2003 | Skujins et al. | |
| 2003/0069529 A1 | 4/2003 | Augustine et al. | |
| 2003/0083643 A1* | 5/2003 | Wilson et al. | 604/523 |
| 2005/0049607 A1* | 3/2005 | Hart et al. | 606/108 |

* cited by examiner

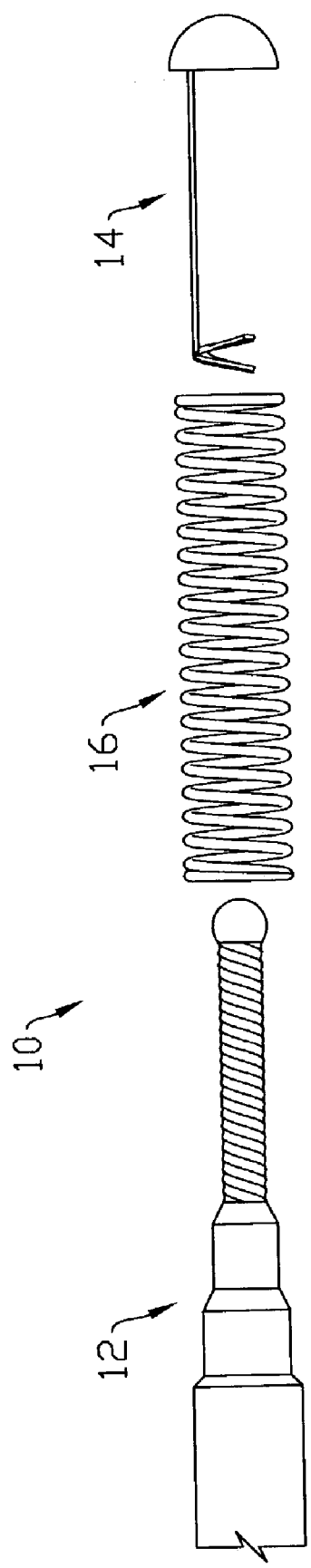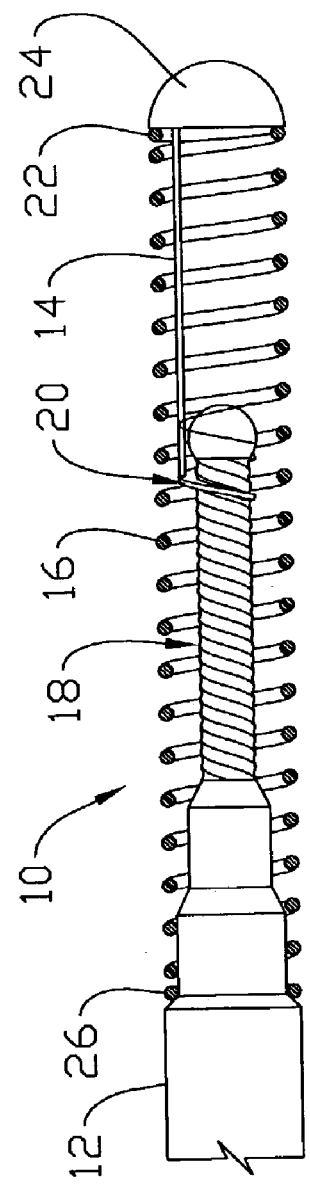

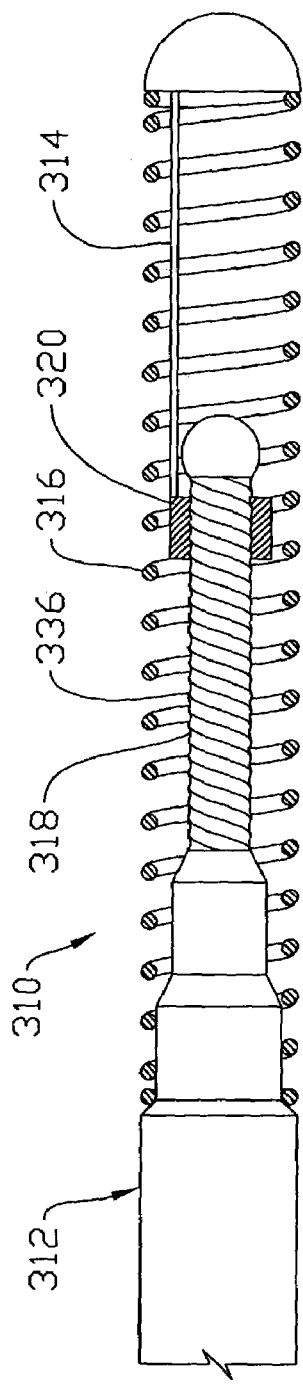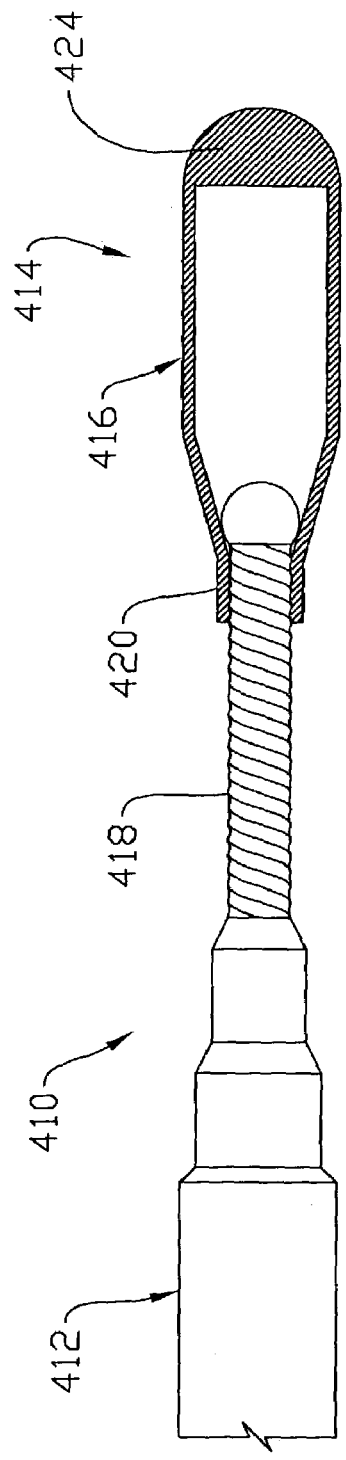

MEDICAL DEVICE WITH CHANGEABLE TIP FLEXIBILITY

FIELD OF THE INVENTION

The present invention relates to improved medical devices and methods of making the same. More particularly, the invention relates to improved elongate shafts with a changeable flexibility.

BACKGROUND

A wide variety of medical devices have been developed for medical use, for example, intravascular use. Some of these devices include an elongate shaft having the desired flexibility adjacent its distal tip. Of the known medical devices with a distal tip, each has certain advantages and disadvantages. There is an ongoing need to provide alternative medical devices with desirable flexibility characteristics.

BRIEF SUMMARY

The invention provides design, material, and manufacturing method alternatives for medical devices with desirable flexibility characteristics. In at least some embodiments, these medical devices include an elongate shaft with a changeable flexibility, for example adjacent the distal tip. These and other desirable features are described in greater detail below.

BRIEF DESCRIPTION OF THE DRAWINGS

FIG. 1 is an exploded view of an example medical device;

FIG. 2 is a partial cross-sectional side view of an example guidewire;

FIG. 9 is a partial cross-sectional side view of another example medical device;

FIG. 10 is a partial cross-sectional side view of another example medical device;

DETAILED DESCRIPTION

Figure 3:
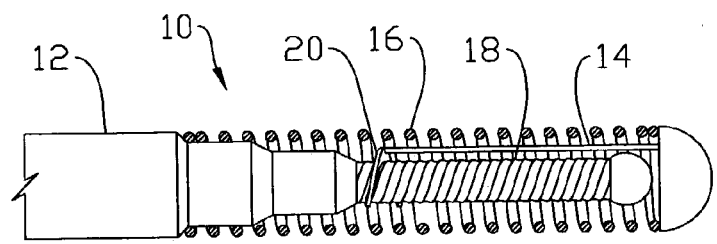
FIG. 3 is a partial cross-sectional side view of an example guidewire having a shortened distal tip.

The following description should be read with reference to the drawings wherein like reference numerals indicate like elements throughout the several views. The detailed description and drawings illustrate example embodiments of the claimed invention.

It may be desirable for medical devices to be available in a variety of different styles and flexibilities. For example, a clinician may wish to utilize a more flexible catheter during some interventions and a less flexible catheter during others. Similarly, it may be desirable to use a number of medical devices with differing flexibilities or for a medical device to be able to alter its flexibility during an intervention. The later may allow the clinician, for example, to alter the flexibility of a medical device and continue using it during a procedure instead of having to use different devices in its place.

FIG. 1 is an exploded view of an example medical device 10 that has a changeable flexibility. Device 10 may include a core member 12, a distal tip member 14, and a sheath or tie member 16. When assembled, the flexibility of medical device 10, for example adjacent tip member 14, can be altered. In at least some embodiments, the flexibility can be altered by shifting the position or configuration of at least one of the components relative to at least one other. For example, the flexibility of device 10 (adjacent tip 14) can be altered by longitudinally shifting the position of tip 14 and/or tie member 16 relative to core member 12. In some embodiments, the longitudinally shifting is selectively reversible, such that the relative positions can be reversible, or changed or altered multiple times. In other embodiments, the longitudinally shifting is not reversible, such that reversion back to an initial position is not possible. These and other embodiments are described in more detail below.

A more detailed account of the structure, features, and benefits of core member 12 and tip member 14 are described below. As to tie member 16, it can be appreciated that a number of forms or configurations may be appropriate for the various embodiments. For example, FIG. 1 depicts tie member 16 as a coil. However, this figure should not be interpreted as limiting tie member 16 to only coils, as a number of other structures may be appropriate. For example, tie member 16 could also be a tubular structure, a polymeric coating, an elastic or expandable member, combinations of these structures, and the like.

Similarly, the material composition of tie member 16 can also vary. For example, tie member 16 may comprise a metal or metal alloy, a polymer, a metal-polymer composite, or essentially any appropriate materials. Additionally, tie member 16 may also be comprised of, coated with, plated with, doped with, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, plastic material loaded with a radiopaque filler, and the like.

FIG. 2 illustrates a partial cross-sectional view of medical device 10, depicted as an assembled guidewire. It should be noted that although this figure depicts device 10 as a guidewire, the invention is not intended to be limited to guidewires. It can be appreciated that device 10 could be any intravascular device or be any device designed to pass through an opening or body lumen. For example, the device may comprise a catheter (e.g., therapeutic, diagnostic, or guide catheter) or other tubular structure, an endoscopic device, a laproscopic device, an embolic protection device, or any other suitable device.

The components of device 10 above may be assembled and/or coupled in essentially any appropriate manner to define device 10 with the desired changeable flexibility. For example, core member 12 and distal tip member 14 may be coupled so that the position of tip member 14 can be longitudinally adjusted relative to core member 12. This feature can be accomplished in a number of ways. For example, core member 12 may include a helical or flanged region 18, and tip member 14 may including a coupling member 20 configured to longitudinally shift or move along flanged region 18.

According to some embodiments, flanged region 18 may comprise a twisted portion of core member 12 and coupling member 20 can be configured to longitudinally shift by following the groove defined by the twist in a manner analogously to how a nut is threaded onto a bolt. In order to alter the flexibility of device 10, a user may simply rotate or otherwise alter the position of core member 12 to allow coupling member 20 to "thread" (i.e., coupling member 20 moving proximally relative to core member 12) or "unthread" (i.e., coupling member 20 moving distally relative to core member 12) along flanged region 18.

FIG. 3 illustrates device 10 where tip member 14 has been shifted proximally. It can be seen from this figure that proximal or distal shifting of tip member 14 can shorten or elongate the length of device 10 adjacent tip member 14. As the length of device 10 adjacent tip member 14 shortens, device 10 generally becomes less flexible at that position and vice versa. Thus, a clinician wishing to decrease the flexibility of device 10 adjacent distal tip member 14 can alter the positioning of the relevant components as prescribed above or in other appropriate manners. Similarly, a clinician may also increase the flexibility by doing the opposite.

It can also be seen that the configuration of tie member 16 may also be altered when altering the flexibility of device 10. For example, some embodiments of tie member 16 include a coil having a pitch. According to these embodiments, shortening the length of device 10 adjacent tip member 14 may result in tightening of the pitch of the coil. This feature may be desirable by allowing outer parameter characteristics of device 10 like outside diameter to remain essentially constant between shortened and elongated configurations of device 10. This feature may also help transfer rotational or other forces applied to core member 12 to tie member 16. This may be desirable because tie member 16 can absorb these forces, for example by altering its pitch or positioning.

Additionally, tie member 16 may be useful as providing a remote location for effectively maintaining the position of tip member 14 while actuating core member 12. For example, the coil embodiment of tie member 16 may include a distal end 22 that is secured to a distal end 24 of tip member 14. Additionally, a proximal end 26 of tie member 16 may be secured to core member 12. Thus, when device 10 is disposed within the vasculature of a patient, a clinician can advance a suitable holding device (e.g., a balloon catheter as will be described in more detail below) over device 10 to grasp and hold tie member 16, and then rotate core member 12. The rotation by the user will allow coupling member 20 to thread or unthread onto core member 12 while the rotational forces applied to core member 12 can be transferred to tie member 16. Because tie member 16 may take the form of a coil, the rotational forces can be absorbed by altering the pitch of the coil as stated above, much like tightening or loosening the windings of a spring.

It can also be appreciated that an alternative way of changing the flexibility of device 10 would be for a user to simply grasp and hold tie member 16 with one hand and rotate core member 12 with the other. Thus, a clinician may be able to determine the desirable flexibility characteristics of device 10 prior to the intervention and then adapt the device to fit the desired flexibility characteristics.

The position and number of the longitudinally shiftable components along the length of device 10 can also be varied. For example, it may be desirable to incorporate flanged region 18 and coupling member 20 at a position besides the distal end of device 10 such as near the middle or the proximal end. In essence, the position of the longitudinally shiftable components can be at any position along the length of device 10. Similarly, two or more longitudinally shiftable component sets may also be included without departing from the spirit of the invention.

Figure 4:
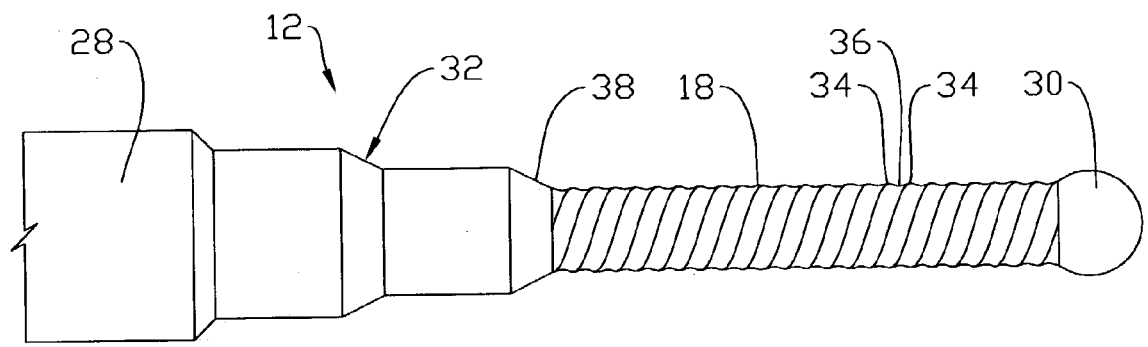
FIG. 4 is a partial cross-sectional side view of a portion of an example core member.

FIG. 4 is an enlarged view of the example embodiment of core member 12 shown previously. Core member 12 may include a proximal region 28, helical or flanged region 18 as stated above (which may generally be distally disposed), and a distal end 30. Core member 12 can be made of any and all suitable materials including metals, metal alloys, polymers, or the like, or combinations or mixtures thereof. Some examples of suitable metals and metal alloys include stainless steel, such as 304v stainless steel; nickel-titanium alloy, such as nitinol, nickel-chromium alloy, nickel-chromium-iron alloy, cobalt alloy, or the like; or other suitable material. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL). In some embodiments, core member 12 or any portion thereof may be comprised of, coated or plated with, or otherwise include a radiopaque material including those described above.

The entire core member 12 can be made of the same material, or in some embodiments, can include portions or sections made of different materials. In some embodiments, the material used to construct core member 12 is chosen to impart varying flexibility and stiffness characteristics to different portions thereof. For example, proximal region 28 and flanged region 18 may be formed of different materials, for example materials having different moduli of elasticity, resulting in a difference in flexibility. In some embodiments, the material used to construct proximal region 28 can be relatively stiff for pushability and torqueability, and the material used to construct flanged region 18 can be relatively flexible by comparison for better lateral trackability and steerability. For example, proximal region 28 can be formed of straightened 304v stainless steel wire, and flanged region 18 can be formed of a straightened super elastic or linear elastic alloy, for example a nickel-titanium alloy wire or ribbon.

In embodiments where different portions of core member 12 are made of different material, the different portions can be connected using any suitable connecting techniques. For example, the different portions can be connected using welding, soldering, brazing, adhesive, or the like, or combinations thereof. Additionally, some embodiments can include one or more mechanical connectors or connector assemblies to connect the different portions of the core wire that are made of different materials. The connector may include any structure generally suitable for connecting portions of a guidewire. One example of a suitable structure includes a structure such as a hypotube or a coiled wire which has an inside diameter sized appropriately to receive and connect to the ends of the proximal portion and the distal portion. Some other examples of suitable techniques and structures that can be used to interconnect different shaft sections are disclosed in U.S. patent application Ser. No. 09/972,276, which is incorporated herein by reference.

The length of core member, or the length of individual portions thereof, are typically dictated by the length and flexibility characteristics desired in the final medical device. In some example embodiments, proximal region 28 may have a length in the range of about 20 to about 300 centimeters and flanged region 18 may have a length in the range of about 3 to about 50 centimeters. It can be appreciated that alterations in the length of core member or portions thereof can be made without departing from the spirit of the invention. In addition, core member 12 can have a solid cross-section as shown, but in some embodiments, can have a hollow cross-section and/or be generally tubular. In yet other embodiments, core member 12 can include a combination of areas having solid cross-sections and hollow cross sections. Moreover, core member 12 or portions thereof, can be made of rounded wire, flattened ribbon, or other such structures having various cross-sectional geometries. The cross sectional geometries along the length of core member 12 can also be constant or can vary.

The core member 12 may include one or more tapered regions 32, for example adjacent flanged region 18. For example, in some embodiments the flanged region 18 may be tapered and have an initial outside size or diameter that can be substantially the same as the outside diameter of the proximal region 28, which then tapers to a reduced size or diameter. For example, in some embodiments, the flanged region 18 can have an initial outside diameter that is in the range of about 0.003 to about 0.020 inches, that tapers to a diameter in the range of about 0.001 to about 0.005 inches. Tapered region 32 may be linearly tapered, tapered in a curvilinear fashion, uniformly tapered, non-uniformly tapered, or tapered in a step-wise fashion. The angle of any such tapers can vary, depending upon the desired flexibility characteristics. The length of the taper may be selected to obtain a more (longer length) or less (shorter length) gradual transition in stiffness. Although FIG. 4 depicts tapered region 32 as being adjacent flanged region 18, it can be appreciated that essentially any portion of core member 12 may be tapered and the taper can be in either the proximal or the distal direction. As shown in FIG. 4, tapered region 32 may include one or more portions where the outside diameter is and portions where the outside diameter remains essentially constant. The number, arrangement, size, and length of the narrowing and constant diameter portions can be varied to achieve the desired characteristics, such as flexibility and torque transmission characteristics.

Tapered region 32 and/or portions thereof may be formed by any one of a number of different techniques, for example, by centerless grinding methods, stamping methods, and the like. The centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing core member 12 during the grinding process. In some embodiments, core member 12 is centerless ground using a Royal Master HI-AC centerless grinder.

As stated above, flanged region 18 may have a number of different configurations. For example, flanged region 18 can be a twisted portion of core member 12. According to this embodiment, twisting of core member 12 defines a number of flanges or threads 34 and a number of valleys 36 between flanges. Alternatively, threads 34 and valleys 36 may be formed by machining a portion of core member 12 similar to creating the threads of a bolt or screw. Either way, flanged region 18 may comprise a region where coupling member 20 may be coupled to core member 12, while allowing for the longitudinal shifting of tip member 14 relative to core member 12.

In at least some embodiments, distal end 30 may include a distal stop. The stop may help to prevent coupling member 20 from traveling too far distally along core member 12 and becoming disengaged therefrom. A number of appropriate forms of a stop may be used without departing from the spirit of the invention. For example, the stop may comprise a solder ball, a metallic or polymeric barrier, or any other suitable structure. Similarly, a proximal stop may also be included. In some embodiments, the proximal stop may take the form of a tapered region of core member 12, indicated by reference number 38. Alternatively, some embodiments of device 10 may include a solder ball stop or other stops similar to those described above, or core member 12 may not include a proximal stop.

Figure 5:
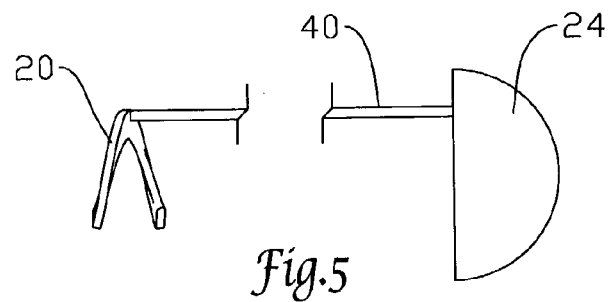
FIG. 5 is a partial cross-sectional side view of an example tip member.

An enlarged view of tip member 14 is shown in FIG. 5. Distal tip member 14 can include coupling member 20 and distal end 24 as described above. A wire or ribbon 40 comprised of any suitable material may extend between coupling member 20 and distal end 24. In general, coupling member 20 can be configured in any appropriate manner so as to allow it to be coupled to core member 12, e.g., adjacent flanged region 18. For example, coupling member 20 may comprise a clip or similar structure that is configured for slidably attaching to or otherwise being disposed within valleys 36 so that it can be longitudinally threaded proximally and distally along flanged region 18. It can be appreciated, however, that a number of variations to coupling member 20 are within the scope of the invention including those described below.

The material composition of tip member 14 and the components thereof may include any of the materials described above. For example, coupling member 20 may comprise a metal, metal-alloy, or polymer. Additionally, any of the components of tip member 14 may be comprised of, plated with, or otherwise include a radiopaque material.

In at least some embodiments, distal end 24 may be disposed adjacent or define the distal end of not only tip member 14 but also device 10. Consequently, it may be desirable for distal end 24 to be comprised of appropriate materials including those that are relatively atraumatic. For example, distal end 24 may be comprised of a polymer, a solder ball, or the like. However, any appropriate material may be used.

Figure 6:
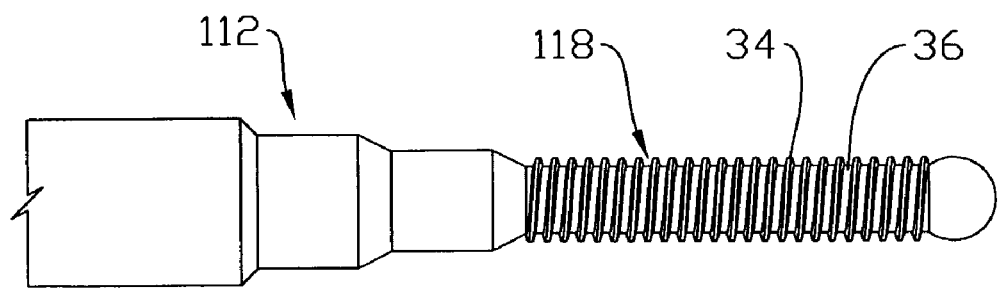
FIG. 6 is a partial cross-sectional side view of a portion of another example core member.

FIG. 6 depicts an alternative example version of core member 112. Core member 112 is similar to core member 12, except that flanged region 118 included one or more threads 134 and a valley region 136 disposed between the windings of threads 134. Accordingly, flanged member 118 is essentially the same as flanged region 18, except that region 118 more expressly includes a structure that is analogous to a threaded nut or screw.

Figure 7:
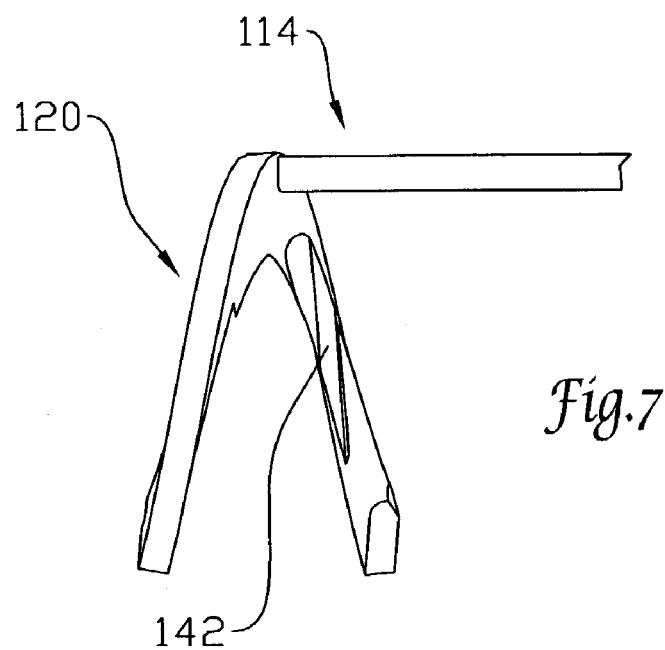
FIG. 7 is a partial cross-sectional side view of a portion of another example tip member.

An example of another tip member 114 including appropriately mating coupling member 120 is shown in FIG. 7. Coupling member 120 is similar to coupling member 20, except that member 120 include mating threads 142 configured to mate with threads 134 of flanged region 118. Threads 142 may allow tip member 114 to be more efficiently coupled to core member 112. It can be appreciated, however, that the structure of tip member 14 may also effectively be used in combination with core member 112.

Figure 8:
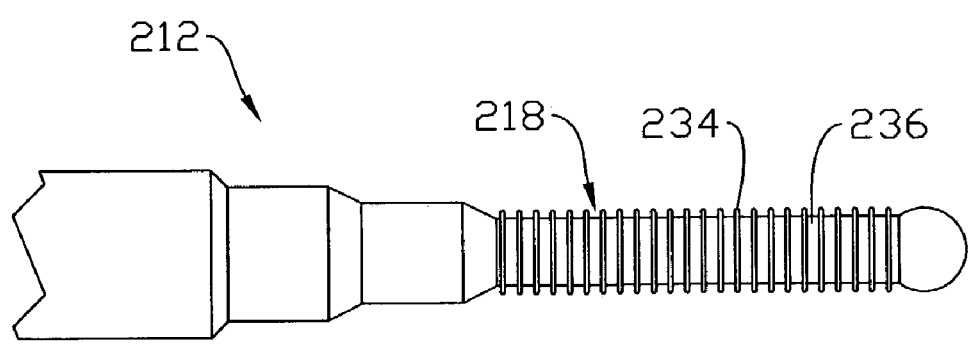
FIG. 8 is a partial cross-sectional side view of a portion of another example core member.

Another example core member 212 is shown in FIG. 8. Core member 212 is similar to core members 12/112 except that flanged region 218 includes a number of radial projections 234 as well as valleys 236 between projections 234. Accordingly, an appropriate coupling member (including coupling members 20/120 or any other suitable form) can be longitudinally shifted by changing the position (i.e., the particular valley 236) that it is disposed in.

Because radial projections 234 may not include a helical arrangement or configuration, longitudinally shifting tip member 14/114 can occur by applying longitudinal force (rather than rotational force) to core member 212. Thus, the clinician can change the position of coupling member 20/120 by simply pushing or pulling on core member 212 while holding the position of tip member 14/114 and/or tie member 16.

An alternative example medical device 310 is illustrated in partial cross-section in FIG. 9. Device 310 and the components thereof (including core member 312, tip member 314, and tie member 316) are similar to any of the structures described herein except that coupling member 320 may be generally tubular. In some embodiments, tubular coupling member 320 may include threads (similar to threads 142 as shown in FIG. 7) disposed on its interior surface to facilitate longitudinal movement along flanged region 318. Alternatively, tubular coupling member 320 may be sized and/or configured to be disposed within valleys 336 of flanged region 318.

Another example medical device 410 is illustrated in partial cross-section in FIG. 9. Device 410 and the components thereof (including core member 412) are similar to any of the like structures described herein except that tip member 414 and tie member 416 are combined into a single, tubular structure. According to this embodiment, tip member 414 may still include coupling member 420 and distal end 424, which may comprise any of the structures or features of analogous structures described above. However, because tip member 414 and tie member 416 can be combined into a tubular structure, tie member 416 is now disposed between tip member 414 and distal end 424.

Figure 11:
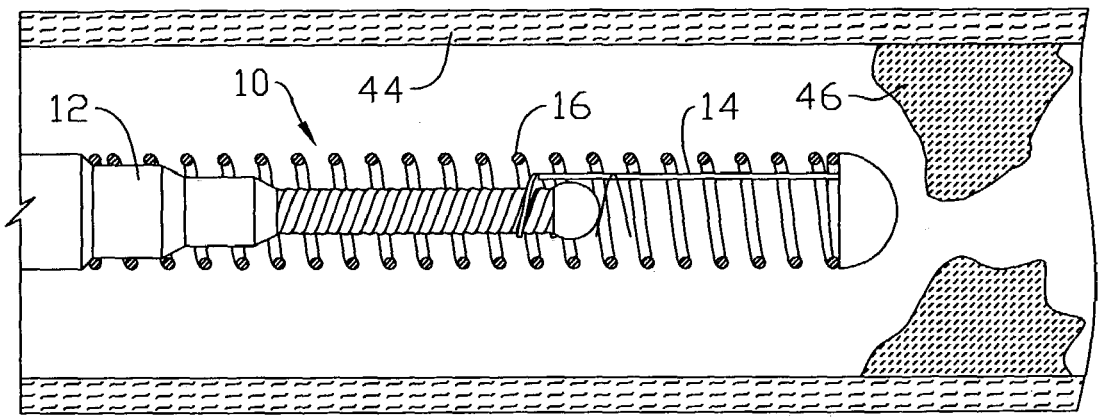
FIG. 11 is a partial cross-sectional plan view of an example medical device disposed in a blood vessel.
Figure 12:
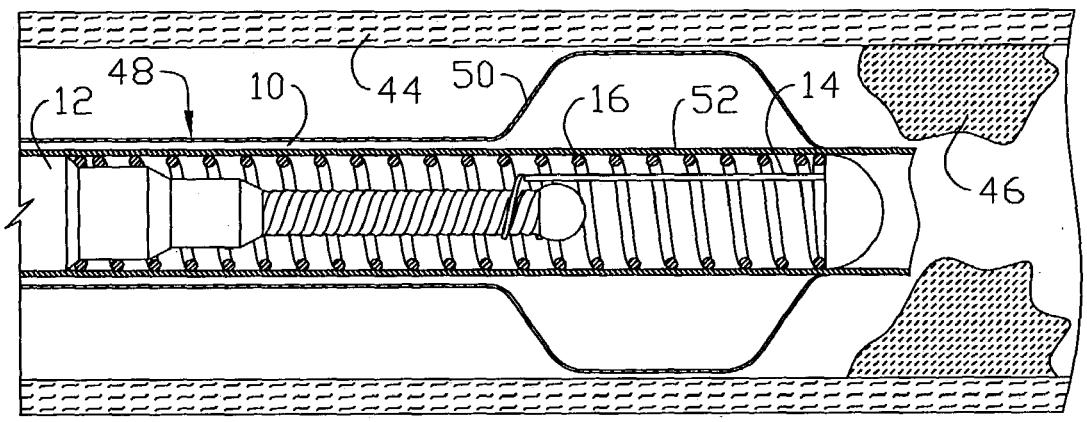
FIG. 12 is a partial cross-sectional plan view of an example medical device and balloon catheter that are disposed in a blood vessel.
Figure 13:
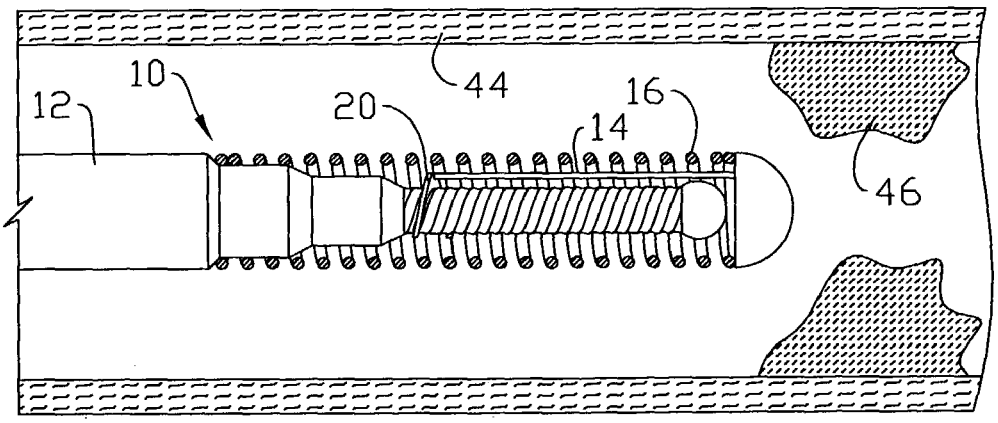
FIG. 13 is a partial cross-sectional plan view of an example medical device with a shortened distal tip that is disposed in a blood vessel.

FIGS. 11–13 illustrate an example of one of the many potential uses of device 10, which is appropriate for any of the devices or alternative forms of the various components described herein. FIG. 11 shows device 10 disposed within a blood vessel 44 adjacent a lesion 46. Because lesion 46 may partially or totally occlude vessel 44, it may be desirable for device 10 to have less distal flexibility in order to allow device 10 to pass lesion 46. Accordingly, it may be desirable to shift the position of tip member 14 relative to core member 12 in order to increase distal stiffness.

One way to increase the distal stiffness would be to remove device 10 from the vasculature and then manually twist core member 12 relative to tip member 14 and/or tie member 16. Alternatively, a catheter 48 and/or a suitable gripping member 50 configured to grip device 10 may be passed over device 10 to an appropriate position adjacent tip member 14. In at least some embodiments, gripping member 50 is an inflatable balloon 50 that may be coupled to catheter 48. According to these embodiments, inflating balloon 50 may exert a force on an interior surface 52, which may be the interior surface of catheter 48 or balloon 50. Thus, balloon 50 may be configured to transfer a grasping force to device 10, for example to tie member 16. It can be appreciated that other appropriate gripping members 50 may be used without departing from the spirit of the invention.

The transfer of force allows tie member 16 and/or tip 14 to be substantially held in place so that core member 12 can be rotated or actuated in the appropriate manner. As a result of the actuation of core member 12, the longitudinal position of tip 14 can be shifted as shown in FIG. 13. The mechanism for the shifting may be similar to what is described above. For example, coupling member 20 may thread along flanged region 18. Additionally, the pitch of coiled tie member 16 may tighten. The shortening of this portion of device 10 may provide device 10 with the desired distal flexibility, which may allow device 10 sufficient stiffness to pass lesion 46. Because portions of device 10 may include radiopaque materials, for example tie member 16, fluoroscopic imaging techniques may allow the clinician to monitor and determine whether device 10 is in the shortened "stiff" configuration or the elongated "floppy" configuration. Moreover, imaging may allow the clinician to precisely alter device 10 to a configuration to a wide range of lengths and flexibilities.

It should also be understood that in some other situations, or in some embodiments, it may be desirable for device 10 to convert to have more distal flexibility. Accordingly, it may be desirable to shift the position of tip member 14 relative to core member 12 in order to decrease distal stiffness. For example, in some embodiments, it may be desirable that the device prior to or during initial insertion into the anatomy of a patient, for example through an introducer structure, has initial distal stiffness and flexibility characteristics that may aid in insertion of the device. After insertion into the anatomy, it may be desirable to convert the device such that it includes a decreased distal stiffness and increased distal flexibility relative to the initial stiffness and flexibility characteristics, for example, to aid in navigation through the anatomy. Such a conversion can take place within the anatomy, for example, as generally described above, but by shifting the device to the elongated "floppy" configuration after insertion.

It should also be understood that in some embodiments, the longitudinally shifting can selectively reversible, such that the relative positions of the working components can be reversible, or changed or altered multiple times. In other embodiments, the longitudinally shifting can be non-reversible, such that reversion back to an initial position is not possible. For example, mechanisms such as cross-threading, flange or thread locking structures, or the like may be used to prevent the device from being moved back into its initial position once longitudinally shifting has taken place.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device, comprising:
   an elongate shaft including a core member, a distal tip member, and a tie member;
   the core member including a proximal region and a distal region;
   the distal tip member including a coupling member and a distal end, the coupling member coupled to the core member adjacent the distal region such that the distal tip is selectively longitudinally movable relative to the core member, and wherein the core member extends proximally from the distal tip member, and the distal tip member extends distally from the core member; and the tie member being disposed over at least a portion of the distal tip member, wherein the tie member is coupled to both the core member and the distal tip member.

2. The medical device of claim 1, wherein the core member includes one or more tapers adjacent the distal region.

3. The medical device of claim 1, wherein the core member is tubular.

4. The medical device of claim 1, wherein the distal region of the core member includes a distal stop.

5. The medical device of claim 1, wherein the distal region includes a plurality of radial flanges.

6. The medical device of claim 5, wherein the radial flanges are formed by outward deflections formed within the distal region.

7. The medical device of claim 5, wherein the coupling includes one or more mating projections adapted for being disposed between two radial flanges.

8. The medical device of claim 5, wherein the coupling is longitudinally slidable along the distal region.

9. The medical device of claim 5, wherein the radial flanges are defined by successive winding of a helical groove disposed about the distal region.

10. The medical device of claim 9, wherein the coupling includes a mating flange adapted to be disposed within the helical groove.

11. The medical device of claim 1, wherein the distal tip includes a wire or ribbon extending between coupling and the distal end.

12. The medical device of claim 1, wherein the tie member includes a sheath.

13. A medical device, comprising:
an elongate shaft including a core member, a distal tip member, and a tie member;
the core member including a proximal region and a distal region;
the distal tip member including a coupling member and a distal end, the coupling member coupled to the core member adjacent the distal region such that the distal tip is selectively longitudinally movable relative to the core member, and wherein the core member extends proximally from the distal tip member, and the distal tip member extends distally from the core member; and
the tie member being disposed over at least a portion of the distal tip member, wherein the tie member includes a coil.

14. The medical device of claim 13, wherein the coil includes a proximal end and a distal end, and wherein the distal end of the coil is attached to the distal tip and the proximal end of the core member.

15. A medical device, comprising:
a core member having a proximal region, a distal region, and a distal stop;
a longitudinally adjustable distal tip coupled to the outer surface of the core member adjacent the distal region, the longitudinally adjustable distal tip including a distal end disposed distally of the core member and a coupling member coupled to the outer surface of the distal region of the core member; and
the distal tip being configured to be selectively adjustable between a first generally elongated position wherein the coupling member is disposed adjacent the distal stop, and a second generally shortened position wherein the coupling member is disposed a distance proximally of the distal stop.

16. The medical device of claim 15, wherein the core member is tubular.

17. The medical device of claim 15, further comprising a tie member coupled to the longitudinally adjustable distal tip.

18. The medical device of claim 17, wherein the distal tip shifts between the first and second positions by longitudinally moving the core member while maintaining the position of the tie member relative to the core member.

19. The medical device of claim 17, wherein the tie member includes a coil.

20. The medical device of claim 19, wherein the coil includes a proximal end and a distal end, and wherein the proximal end is attached to the core member and the distal end is attached to the distal tip.

21. The medical device of claim 19, wherein the coil has a first pitch when the distal tip is in the first position and a second pitch when the distal tip is in the second position, the first pitch being greater than the second pitch.

22. The medical device of claim 17, wherein the tie member includes a tube.

23. A medical device, comprising:
a core member having a proximal region, a distal region, and a distal stop, wherein the distal region includes a plurality of radial flanges;
a longitudinally adjustable distal tip coupled to the core member adjacent the distal region, the longitudinally adjustable distal tip including a distal end and a coupling member coupled to the distal region of the core member; and
the distal tip being configured to be selectively adjustable between a first generally elongated position wherein the coupling member is disposed adjacent the distal stop, and a second generally shortened position wherein the coupling member is disposed a distance proximally of the distal stop.

24. The medical device of claim 23, wherein the radial flanges are formed by outward deflections formed within the distal region.

25. The medical device of claim 23, wherein the coupling member includes one or more mating projections adapted for being disposed between two radial flanges.

26. The medical device of claim 23, wherein the radial flanges are defined by successive winding of a helical groove disposed about the distal region.

27. The medical device of claim 26, wherein the coupling member includes a mating flange adapted to be disposed within the helical groove.

28. A medical device, comprising:
a core member having a proximal region, a distal region, and a distal stop;
a longitudinally adjustable distal tip coupled to the core member adjacent the distal region, the longitudinally adjustable distal tip including a distal end and a coupling member coupled to the distal region of the core member; and
a tie member coupled to the longitudinally adjustable distal tip;
wherein the distal tip being configured to be selectively adjustable between a first generally elongated position wherein the coupling member is disposed adjacent the distal stop, and a second generally shortened position wherein the coupling member is disposed a distance proximally of the distal stop, and wherein the distal tip shifts between the first and second positions by rotating the core member while maintaining the position of the tie member relative to the core member.

29. A medical device, comprising:
a core member having a proximal region and a distal region; and
a longitudinally adjustable distal tip member non-releasably coupled to the core member adjacent the distal region, the distal tip member being configured to reversibly shift between a first generally elongated position and a second generally shortened position, wherein the core member extends proximally from the distal tip member, and the distal tip member extends distally from the core member.

30. The medical device of claim 29, further comprising means for shifting the distal tip member between the first and second positions.

31. A medical device, comprising:
a core member having a proximal region and a flanged region;
a longitudinally adjustable distal tip member disposed adjacent the flanged region, the distal tip member being configured to selectively shift between a first generally elongated position and a second generally shortened position, wherein the core member extends proximally from the distal tip member, and the distal tip member extends distally from the core member;
means for coupling the distal tip member to the flanged region; and
means for shifting the distal tip member between the first and second positions, wherein the distal tip member is non-releasably coupled to the core member.

32. A method of altering the length of a portion of a medical device, the method comprising:
providing a medical device including a core member having a proximal region, a distal region, and a distal stop; a longitudinally adjustable distal tip member coupled to the core member adjacent the distal region, the longitudinally adjustable distal tip member including a distal end and a coupling member coupled to the distal region of the core member; and the distal tip member being positioned in a first position and being configured to selectively shift between the first position and a second position;
advancing the medical device through a body lumen to a target location;
advancing a gripping member over the medical device so that gripping member is positioned adjacent the distal tip member;
gripping the medical device with the gripping member adjacent the distal tip member; and
altering the position of the core member such that the distal tip shifts from the first position to the second position.

33. The method of claim 32, wherein the gripping member includes an inflatable member coupled to a catheter, and wherein the step of gripping the medical device with the gripping member includes inflating the inflatable member.

34. The method of claim 32, wherein the step of altering the position of the core member such that the distal tip shifts from the first position to the second position includes rotating the core member.

35. The method of claim 32, wherein the step of altering the position of the core member such that the distal tip shifts from the first position to the second position includes longitudinally pushing or pulling the core member.

36. A medical device, comprising:
an elongated core member including a proximal region and a distal region; and
a distal tip member including a distal end and a non-releasable coupling coupled to the core member adjacent the distal region of the core member for selective longitudinal adjustment of the positioning of the non-releasable coupling along the distal region of the core member, wherein the core member extends proximally from the distal tip member, and the distal tip member extends distally from the core member.

37. The medical device of claim 36, wherein selective adjustment of the longitudinal position of the coupling along the distal region of the core member selectively adjusts the length of the medical device.

* * * * *